United States Patent [19]

McKenzie

[11] Patent Number: 5,260,277

[45] Date of Patent: Nov. 9, 1993

[54] GUANIDINYL AND RELATED CELL ADHESION MODULATION COMPOUNDS

[75] Inventor: Thomas C. McKenzie, Cardiff, Calif.

[73] Assignee: Tanabe Seiyaku Co., Ltd., Osaka, Japan

[21] Appl. No.: 579,789

[22] Filed: Sep. 10, 1990

[51] Int. Cl.$^5$ .................. A61K 37/02; C07K 5/08; C07K 5/10
[52] U.S. Cl. .................. 544/18; 514/20; 530/331
[58] Field of Search ............ 514/18, 20; 530/331

[56] References Cited

U.S. PATENT DOCUMENTS

| | | | |
|---|---|---|---|
| 4,879,313 | 11/1989 | Tjoeng et al. | 514/20 |
| 4,952,562 | 8/1990 | Klein et al. | 514/18 |
| 5,053,392 | 10/1991 | Klein et al. | 514/18 |
| 5,053,393 | 10/1991 | Tjoeng et al. | 514/18 |
| 5,061,693 | 10/1991 | Nutt et al. | 514/17 |

Primary Examiner—Lester L. Lee
Attorney, Agent, or Firm—Spensley Horn Jubas & Lubitz

[57] ABSTRACT

Guanidinyl-containing compounds, and related compounds and salts, useful as cell receptor antagonists for modulating cell adhesion via integrin receptors and/or fibronectin receptors, are disclosed. Methods for synthesizing, testing, formulating, and using the compounds as therapeutic agents are also disclosed.

12 Claims, 1 Drawing Sheet

FIG. 1

GUANIDINYL AND RELATED CELL ADHESION MODULATION COMPOUNDS

I. FIELD OF INVENTION

The present invention relates to novel guanidinyl and related compounds which are characterized by cell adhesion modulation activity. The compounds have application to the study and treatment of disease conditions mediated by cell adhesion. Specifically, the compounds have application to the study, diagnosis, treatment or prevention of diseases and conditions such as, for example, cardiovascular disease, harmful platelet aggregation, neoplastic disease including metastasis of neoplastic growth, wound healing, inflammation and autoimmune disease or other diseases or conditions involving cell adhesion.

II. BACKGROUND OF THE INVENTION

The extracellular matrix is that material which surrounds the muscle and is the major component of connective tissue of all mammals. The extracellular matrix provides for structural integrity, and promotes cell migration and cellular differentiation. As part of these functions, the extracellular matrix has been shown to support adhesion for various types of cells in vitro. Molecules such as the collagens, fibronectin, vitronectin, laminin, von Willebrand factor, thrombospondin, bone sialoprotein, fibrinogen, and tenacin have been found to possess this property of mediating cell adhesion.

The above cell-adhesive molecules have been found to exhibit a structual similarity in their respective binding sites, each of which contains the amino acid sequence arginine-glycine-aspartic acid, or RGD using conventional single letter nomenclature. The cell-binding site in fibronectin has been reproduced synthetically. In turn, the cellular receptor site for fibronectin has been identified for various cells. In addition, cellular receptors that recognize RGD-containing sequences in other extracellular matrix proteins (e.g., the vitronectin receptor) have been identified.

Such cellular receptors, responsive to RGD-containing proteinaceous compounds, have been characterized. The complete, primary structure of the fibronectin receptor has been deduced from cDNA, and physical properties have been determined. Argraves, et al., *J.Biol. Chem.*, 261: 12922 (1986); Argraves et al., *J. Cell Biol.*, 105: 1183 (1987). The protein exists at the cell surface as a heterodimeric complex (although the larger polypeptide is enzymatically processed) having both polypeptide chains inserted into the membrane. Each chain extends 30–40 residues into the cytoplasmic space, and at least one of the cytoplasmic peptides appears to interact with the cytoskeleton. Horwitz et al., *Nature*. 320: 531 (1986). The larger of the two polypeptides, the α subunit, contains a number of regions that are structurally similar to calmodulin and that apparently mediate the binding of calcium to the receptor. The presence of such divalent cations is required for the receptor to bind ligand. The β subunit is somewhat smaller and conformationally compact due to numerous intrachain disulfide bonds. The cytoplasmic domain of the β subunit contains a potentially phosphorylated tyrosine. Hirst et al., *PNAS-USA*, 83: 6470 (1986); Tamkun et al., *Cell*, 46: 271–282 (1986).

Other RGD-directed receptors, as well as other "orphan" receptors the ligand for which is unknown, have also been characterized. This putative RGD commonality of the ligand matrix proteins has revealed a superfamily of cell surface receptor proteins that share a high degree of structural similarity and probably also functional similarity. The members of this superfamily of cell surface proteins collectively are known as the integrins. The integrins can be grouped on the basis of the identity of their β subunit. The β subunit, as disclosed above for the fibronectin receptor, is compact due to a high degree of cross-linking. The first group of integrins includes the very late activation antigen (VLA) proteins, which themselves include the fibronectin receptor (VLA-5), the collagen receptor (VLA-2), and the laminin receptor. The second group includes the lymphocyte associated antigen-1 (LFA-1), macrophage antigen-1 (MAC-1), and p150,95. The third group includes the vitronectin receptor, and platelet glycoprotein gpIIb/IIIa. Hynes, *Cell*, 48: 549 (1987); Hemler, *Immunol. Today*, 9: 109 (1988); Springer et al., *Annu. Rev. Immunol.*, 5: 223 (1987); Kishimoto et al., Leukocyte Integrins, in: Leukocyte Adhesion Molecules, T. A. Springer, D. C. Anderson, A. S. Rosenthal, and R. Rothlein, Eds., Springer-Verlag, New York, pp. 7–43 (1989).

The RGD-directed receptor present on platelets that binds fibronectin, vitronectin, fibrinogen, and von Willebrand factor has also been purified. This receptor is the gpIIb/IIIa protein complex. This receptor is thus not specific to one extracellular matrix protein, as are the above fibronectin and vitronectin receptors. It has been proposed that this lack of specificity is correlated to the lack of conformational specificity in the ligands. Other work has suggested that specificity ca be achieved with relatively short, conformationally restricted synthetic pep-tides containing the RGD sequence. For a literature summary, see: Pierschbacher et al., *Nature*, 309: 30 (1984); Pierschbacher et al., *PNAS-USA*, 81: 5985 (1984); Ruoslahti et al., *Cell*, 44: 517 (1986); Pierschbacher et al., *Science*, 238: 491 (1987); Pierschbacher et al., *J.Biol.Chem.*, 262: 17294 (1987); Hynes, *Cell*, 48: 549 (1987); Ruoslahti, *Ann. Rev. Biochem.*, 57: 375 (1988). It has also been proposed that the receptor affinity for its peptide ligand may be altered as the stereoconformation, or three-dimensional shape, of the peptide is restricted, typically by cyclization. Pierschbacher and Ruoslahti, PCT International Publication WO 89/05150 (1989).

A limited number of compounds containing sequences of natural amino acids or derivatives other than RGD may also possess the capability for affecting cell adhesion. These non-RGD-containing peptides are not well characterized. See, Graf, J. et al., *Cell*, 48:989 (1987); Kloezewiak, M. et al., *Biochemistry*, 23:1767–1774 (1984); Wayner, E. A., et a)., *J. Cell. Biol.*, 109:1321 (1989).

U.S. Pat. No. 4,879,313 to Tjoeng, et al. reports the utility as platelet aggregation inhibitors of certain peptide mimetic compounds containing, in addition to a guanidinyl group at one terminus and an internal aspartic acid residue, an aromatic structure (phenyl, biphenyl, naphthyl, pyridyl or thienyl groups, and certain methoxy-substituted forms thereof) at another defined position in the compound. Related structures containing an internal glycine residue are reported in U.S. Pat. No. 4,857,508 (Adams, et al.).

All publications, patents and other reference materials to which reference is made in the present specification are incorporated herein by reference.

III. SUMMARY OF THE INVENTION

The present invention relates to compounds having activity as cell adhesion modulators. The compounds are characterized by the presence of a guanidinyl or related group (e.g., substituted guanidinyl, urea or thiourea group) linked through a hydrocarbon moiety, and optionally also through an amino acid residue, to a carboxyl- or carboxyl-derivative-containing portion comprising an aspartic acid-related residue and, optionally, an additional amino acid residue or analog thereof. The carboxyl or carboxyl-derivative portion of the compounds may have either a normal- or a reverse-orientation peptide bond structure, and (especially in the latter case) may contain one or more D-enantiomer residues.

The compounds, in one aspect, sufficiently mimic extracellular matrix ligands or other cell adhesion ligands so as to bind to cell surface receptors. Such receptors include integrin receptors in general, including the fibronectin, collagen, laminin, LFA-1, MAC-1, p150,95, vitronectin and gpIIb/IIIa receptors. The novel compounds have been found to modulate cell adhesion by competing, for example, with RGD-containing ligands and by binding to RGD-directed receptors on cell surfaces. Such cell adhesion ligands, including (but not limited to) fibronectin, are sufficiently inhibited from binding to the cell's receptor as to prevent or reduce cell adhesion. Other uses include enhancing cell adhesion by using the compounds to attach cells to a surface, or by other promotion of cell adhesion. The useful compounds herein described function as cell-adhesion modulators.

One object of the present invention is to provide novel compounds which act to modulate cell adhesion.

Another object of the present invention is to provide novel guanidinyl and related compounds which are capable of binding with a cellular receptor.

Another object of the present invention is to provide novel guanidinyl and related compounds which contain one or more "reverse" amino acid residues and which are capable of binding to a cellular receptor.

Another object of the present invention is to provide a novel method for modulating cell adhesion using novel compounds.

Another object of the present invention is to provide novel compounds, formulations, and methods which may be used in the study, diagnosis, treatment or prevention of diseases and conditions which relate to cell adhesion, including but not limited to rheumatoid arthritis, asthma, allergies, adult respiratory distress syndrome (ARDS), cardiovascular disease, thrombosis or harmful platelet aggregation, neoplastic disease including metastasis of neoplastic growth, wound healing, Type I diabetes, inflammatory conditions including ophthalmic inflammatory conditions and inflammatory bowel disease (e.g, ulcerative colitis and regional enteritis), and autoimmune diseases.

Another object is to provide derivative compounds, such as, but not limited to, antibodies and anti-idiotype antibodies to the compounds disclosed and claimed in order to study, diagnose, treat or prevent diseases and conditions which relate to cell adhesion, including but not limited to rheumatoid arthritis, asthma, allergies, adult respiratory distress syndrome (ARDS), cardiovascular disease, thrombosis or harmful platelet aggregation, neoplastic disease including metastasis of neoplastic growth, wound healing, Type I diabetes, inflammatory conditions and autoimmune diseases.

V. DETAILED DESCRIPTION

The compounds of the present invention are those having the property of modulating cell adhesion.

While cell adhesion is required for certain normal physiological functions, situations exist in which cell adhesion is undesirable, or in which modulated cell adhesion is desirable.

Altered leukocyte-endothelial interactions are implicated in adult respiratory distress syndrome (ARDS). Here, the attachment of inappropriate cells to the lung lining induces an inflammatory response. This results in lung injury, ARDS and in some cases, asthma. Preliminary in vitro results show that such detrimental attachment, in which the leukocyte adheres to endothelial cells or the lung extracellular matrix, is mediated by RGD-containing protein and RGD-recognizing receptors on the leukocytes. In this situation, peptides or other compounds with a binding affinity to RGD receptors are desirable as competitive antagonists and should be useful in treating ARDS and asthma. Such compounds are disclosed herein.

Cell adhesion also contributes to metastasis of cancerous tumors. Metastasis has been called "the major underlying cause of death from cancer." Welch, et al., *Intern. J. Cancer,* 43: 449 (1989). An RGD-containing peptide which would prevent cell adhesion to basement membrane components may be useful to prevent or eliminate metastasis. See, Humphries, M. J. et al., *Science,* 233:467 (1986); Liotta, L. A., *Cancer Res.,* 46:1 (1986); Roose, E., *Biochem. Biophys. Acta.,* 738:263 (1986). A peptide or other compound with suitable affinity for RGD receptors, such as disclosed herein, should likewise have anti-metastasis utility.

Harmful blood clotting is also caused by inappropriate cell adhesion, particularly cell adhesion to the extracellular matrix. The attachment, spreading and aggregation of platelets on extracellular matrices are central events in thrombus formation. These events can be regulated by the family of platelet adhesive glycoproteins, fibrinogen, fibronectin, and von Willebrand factor. Fibrinogen functions as a cofactor for platelet aggregation, while fibronectin supports platelet attachment and spreading reactions. Von Willebrand factor is important in platelet attachment to and spreading on subendothelial matrices. Plow et al., *PNAS-USA,* 82: 8057 (1985). A peptide or other compound, such as these herein, which would function as an antagonist and bind to cell receptors which recognize the matrix glycoprotein RGD site would be beneficial as a thrombolytic.

Other physiological conditions may be treated by stimulatory modulation of cell adhesion. Wound healing, for example, is undesirably prolonged when insufficient cell adhesion occurs. A peptide or other compound with suitable affinity for RGD receptors, attached for example to a suitably positioned matrix or surface, may be able to promote beneficial cell adhesion and resultant wound healing by binding cells with the appropriate RGD-recognizing receptor. Also, in prosthetic implantation, such peptides or other compounds coating the prosthesis would provide a means for covering the prosthesis with a surface of cells. This cell surface would provide a surface compatible with the organism, and thus minimize rejection that might otherwise occur due to stimulation of the immune system by the prosthesis itself. The compounds of the present invention are believed to be useful in this cell adhesion modulation application as well.

The cell adhesion modulation compounds of the present invention are represented in part herein by amino acid residues wherein the individual amino acids are represented by their standard three-letter abbreviations as follows:

| Amino Acid | Three-letter symbol |
|---|---|
| Alanine | Ala |
| Arginine | Arg |
| Asparagine | Asn |
| Aspartic acid | Asp |
| Cysteine | Cys |
| Glutamine | Gln |
| Glutamic acid | Glu |
| Glycine | Gly |
| Histidine | His |
| Isoleucine | Ile |
| Leucine | Leu |
| Lysine | Lys |
| Methionine | Met |
| Phenylalanine | Phe |
| Proline | Pro |
| Serine | Ser |
| Threonine | Thr |
| Tryptophan | Trp |
| Tyrosine | Tyr |
| Valine | Val |

Where abbreviations such as the foregoing are used herein without an indication of enantiomeric structure, either the L- or D-enantiomers may suitably be utilized, although the L-enantiomer is preferred for amino acids having the normal (non-reversed) peptide bond orientation, and the D-enantiomer is preferred for amino acids having a reversed orientation (see discussion below).

Additional abbreviations used herein include:

| β-Ala | β-Alanine (3-aminopropionic acid) |
|---|---|
| BOC | tert-butyloxycarbonyl |
| Cbz | Benzyloxycarbonyl |
| DCC | Dicyclohexylcarbodiimide |
| DCHA | Dicyclohexylamine |
| DIEA | Diisopropylethylamine |
| DMF | Dimethylformamide |
| FMOC | Fluorenylmethyloxycarbonyl |
| iPr | Isopropyl |
| Nle | Norleucine |
| NMM | N-methylmorpholine |
| Sar | Sarcosine |
| THF | Tetrahydrofuran |

The first group of compounds of this invention are of the formula:

wherein

Y is an unsubstituted or substituted, linear or branched linking moiety selected from saturated and unsaturated hydrocarbon groups containing from 1 to about 15 linking atoms, and optionally containing one or more heteroatoms and/or one or more cyclic structures;

Z is optional and, where present, is selected from Gly (most preferably), and from Ala, Sar and β-Ala;

$R^1$ and $R^2$ are independently substituents selected from —OR (including hydroxyl), —NR$_2$ (including —NH$_2$ and —NHR), —NHNH$_2$ and —SR, and where one of $R^1$ and $R^2$ may additionally be selected from wherein $R^3$ is a substituent selected from —OR (including hydroxyl), —NR$_2$ (including —NH$_2$ and —NHR), —NHNH$_2$ and —SR, and $R^4$ is a substituent selected from groups of the form —R and acyl groups —COR;

n and (where present) m are independently 1, 2 or 3; and wherein each R is individually a pharmaceutically suitable substituent group, preferably one selected from hydrogen, from linear and branched, unsubstituted and substituted C$_1$-C$_8$ lower alkyls, C$_2$-C$_8$ alkenyls, C$_2$-C$_8$ alkynyls, C$_6$-C$_{14}$ aryls, C$_7$-C$_{14}$ alkaryls, C$_7$-C$_{14}$ aralkyls and C$_3$-C$_{14}$ cycloalkyls, from heteroatomic groups and, in the case of —NR$_2$, from cyclized groups forming (in attachment with the nitrogen atom) a 5-8 membered heterocyclic ring optionally containing oxygen, nitrogen or sulfur as a further ring heteroatom.

The compounds of the invention further include pharmaceutically acceptable base- or acid-addition salts of the compositions of Formula I. The pharmaceutical compositions of the invention include such compounds (including salts thereof) formulated with a pharmaceutically acceptable excipient.

It will be seen that the X substituent of the form RN=, as well as the substituents $R^1$, $R^2$ and (where present) $R^3$ and $R^4$, are in turn each independently defined in terms of a further substituent R. With respect to these latter substituents designated as R, hydrogen, as well as unsubstituted and substituted lower alkyl and single-ring aryl (including single-ring aralkyl and alkaryl) hydrocarbon moieties, are most generally preferred. Methyl, ethyl, isopropyl, tert-butyl and benzyl are examples of such preferred hydrocarbon substituents, with benzyl ($-CH_2(C_6H_5)$) being a particularly preferred aralkyl substituent. Homoatomic polycyclic structures such as naphthalene, decalin, anthracene or phenanthrene may also be employed, although single-ring structures are presently preferred for cyclic substituents. Each R group in the compound may be independently selected, and need not be the same in each position in the compound.

Where R in such cases is chosen to be a heterocyclic group, the cyclic structure may contain one or more heteroatoms selected from N, O and S, and may be mono- or polycyclic. The cyclic structure can be saturated, as in morpholinyl, thiomorpholinyl, piperidinyl, piperazinyl, pyrrolidinyl, pyrazolidinyl, quinuclidinyl, imidazolidinyl, and other structures, or unsaturated or aromatic, as in imidazolyl, pyridyl, pyrazinyl, pyrimidinyl, pyrazolyl, pyrrolyl, pyrrolinyl, pyridazinyl, pyrrodiazolyl, isothiazolyl, thienyl, thiazinyl, isoxazolyl, furazanyl and other structures. Polycyclic structures such as indolyl, quinolyl, quinazolinyl, phenoxazinyl, phenazinyl, phenothiazinyl, benzo[b]thienyl, phenanthrolinyl or others may be employed. Attachment of such cyclic R groups with the remainder of the compound may occur through a carbon or (provided that a point of bonding is present on a heteroatom) through a heteroatom within the heterocyclic group, or attachment may be achieved through, for example, an intermediate alkylene moiety which links the cyclic group with the remainder of the compound. Such cyclic R groups may also be substituted with pharmaceutically suitable substituents as is now discussed.

Where one or more of the R groups in the compound is itself additionally substituted, preferred substituents include hydroxyl, amino, lower ($C_1$-$C_8$) alkoxyl and alkyl, and, in the case particularly of aromatic R groups, the foregoing substituents as well as nitro and halogen (especially chloro and bromo) moieties. Such substituents on R may be used, for example, to alter bioactivity, solubility and/or biodistribution characteristics of the subject compounds. Where R includes an aryl group, substituents occurring on the meta and/or para positions (i.e., 3'- and/or 4'-positions) are most preferred. Preferred alkaryl forms of R thus include (3'-methyl)-phenyl and (4'-methyl)phenyl groups. Multiply-substituted aryls, particularly where the substituent is small as in methyl or halo, are also useful. These preferred substituents on the R groups are also preferred for structures of the invention described hereinafter.

With regard particularly to the X-position, the most preferred substituent is of the form RN= (i.e., wherein the heteroatom nitrogen is double-bonded to the adjacent carbon). The preferred R substituents in this position are as discussed above, with hydrogen being most highly preferred (so as to yield an unsubstituted guanidinyl moiety). Lower alkyl and single-ring aryl (including single-ring aralkyl and alkaryl) moieties are also preferred. Oxygen- and sulfur-containing analogs of guanidinyl moieties, wherein X= is O= or S= (hereinafter referred to "guanidinyl analogs," specifically of a urea or thiourea form), may also be employed.

With regard particularly to the substituents $R^1$, $R^2$, $R^3$ and $R^4$, those of the form —OR, with choices of R therein yielding hydroxyl substituents (i.e., R is hydrogen), as well as those yielding unsubstituted and substituted lower alkoxy and single-ring aryloxy, and unsubstituted and singly-substituted lower alkylamino substituents, are preferred. As noted above, R may be the same or different in each position in $R^1$, $R^2$, $R^3$ and $R^4$. Where such a substituent yields a structure of the form —OR other than hydroxyl (i.e., R is other than hydrogen), structures of the form $-OCH_3$, $-OCH_2(C_6H_5)$ and $-O(C_6H_5)$ (i.e., $-R$ is $-CH_3$, $-CH_2(C_6H_5)$ or $-C_6H_5$) are especially preferred and are believed to protect the resultant compound from metabolism in the in vivo environment, and may also tend to enhance the ability of the compound to interact with receptor sites on cells or other structures in the body, thereby increasing the activity of the compound. Likewise, where $R^1$, $R^2$ and/or $R^3$ are of the form $-NR_2$, amidating substituents such as those of the form $-NH_2$, $-NHCH_3$ and $-NHCH_2CH_3$ (i.e., each —R is hydrogen, or one —R is hydrogen and the other is $-CH_3$ or $-CH_2CH_3$), and amidating substituents wherein the nitrogen is itself substituted with one or two aromatic groups (i.e., one or two R groups in $-NR_2$ is of an aryl, alkaryl or aralkyl form as defined above) are preferred.

With respect to $R^1$, $R^2$, and $R^3$, bulky esterifying groups, such as aromatic esterifying groups, of the form —OR are particularly preferred, and the benzyloxy ($-OCH_2(C_6H_5)$) group is particularly preferred for each of $R^1$, $R^2$ and $R^3$. Similarly, with respect to $R^4$, it is especially preferred that R therein be an aromatic group, particularly benzyl or benzoyl. As described above, substituents on such aromatic groups including hydroxyl, amino, lower alkoxyl and alkyl substituents, and especially electron-withdrawing substituents such as halogen and nitro groups, are useful in one or more positions on the aromatic structure. Examples of preferred substituents (aromatic and otherwise) in these positions include those wherein R is p-chlorobenzyl, benzyloxymethyl, trityl (triphenylmethyl), t-butyl, cinnamyl, other substituted benzyl or substituted methyl, alkyl, cycloalkyl, phenyldimethylsilyl, t-butyldimethylsilyl and triisopropylsilyl.

Where an amidating group of the structure $-NR_2$ is to be cyclic in form, the N-morpholinyl heterocyclic structure is preferred. Where one or more R groups in such a structure includes an aromatic group, each may be further substituted in one or more positions as described above. Unsubstituted or substituted benzyl substituents ar particularly preferred in such structures.

The $R^2$ substituent, or alternately the $R^1$ substituent, may comprise, in addition to a portion containing a group of the form R as described above, an amino acid structure chosen from various amino acid residues as well as analogs thereof. As an example of one such form of $R^2$ (or $R^1$), the structure —Val-$R^3$ set forth above defines a carboxyl-substituted form of the amino acid valine, wherein the carboxyl-substituent is $R^3$ as defined above. Where $R^3$ is chosen to be hydroxyl (as in —Val-OH), the resulting $R^2$ group is the amino acid valine. Similarly, $R^3$ may be chosen to be an esterifying or amidating group (as in, e.g., —Val-OR, —Val-$NH_2$ or —Val-NHR), wherein R is chosen as described above and is preferably a lower alkyl or single-ring aryl (e.g., benzyl or phenyl) group. Likewise, $R^2$ (or $R^1$) groups of the form —Ala-$R^3$, —Leu-$R^3$, —Ile-$R^3$, —Nle-$R^3$ and —Thr-$R^3$ refer to the carboxyl-substituted amino acids alanine, leucine, isoleucine, norleucine, and threonine, wherein R³ may be hydroxyl or other substituent as described above.

The groups as used above with respect to R² (or R¹) define carboxyl-substituted serine and threonine moieties having, additionally, a substituent R⁴ on the oxygen of the amino acid side chain. Serine-derived moieties are particularly preferred in this position. Where R⁴ in the above formula is chosen to be hydrogen, and R³ is hydroxyl, a simple serine or threonine moiety results.

The other forms recited in Formula I above for R² (or R¹) represent analogs of serine wherein the side chain and/or the carboxylate group of the amino acid has been modified or truncated. Serine is especially preferred as the R² substituent, particularly when substituted at R³ and/or R⁴ (most preferably in both positions) with a bulky substituent for R therein. As noted above, it is especially preferred in such structures that the substituent R⁴ on the side chain position be selected from bulky substituents including for example, benzyl, p-chlorobenzyl, benzyloxymethyl, trityl (triphenylmethyl), t-butyl, cinnamyl, other substituted benzyl, substituted methyl, alkyl, cycloalkyl, phenyldimethylsilyl, t-butyldimethylsilyl and triisopropylsilyl groups, with the benzyl group (forming a side chain ether functionality) being especially preferred. Acyl substituents, including lower acyl substituents such as acetyl groups, are also useful.

As will be discussed in more detail below, the linking moiety Y is preferably selected in conjunction with the other portions of the claimed compounds (most particularly the optional group Z, and the methylene moieties enumerated by the integer n) in a manner which provides suitable spacing between the guanidinyl (or guanidinyl-analog) group and the carbonyl-containing group designated as —COR¹. When the linking moiety Y is of a hydrocarbon chain form, the preferred length of the linking portion of the chain is from about 2 to about 5 methylene or other atomic residues (noninclusive of carbons or other groups appended as branches or substituents to the linking portion of the alkyl chain). Simple alkylene chains of the form —(CH₂)ᵣ—, wherein r is an integer of from 1 to about 8, and preferably 1 to about 5 where the optional Z group is not present, are preferred for the linking group Y. Such chains may be used to yield des-α-amino forms of arginine and homologs thereof in the structures of the present compounds.

As used herein, the "linking portion" of Y refers to that portion of Y which effectuates the intramolecular spacing between the two residues of the compound adjacent to the Y group, i.e., the guanidinyl (or guanidinyl-analog) residue bonded to the left of Y and the residue bonded to the right of Y. Thus, portions of Y which do not contribute to this inter-residue spacing within the subject compounds, such as branch groups or substituents as in, for example, are not to be considered a part of the linking portion of Y. Accordingly, in the examples of Y depicted above, the linking portions affording spacing between the adjacent residues in the compound comprise, respectively, 4 linking atoms —C—O—C—C— and 5 linking atoms (—C—C—C—C—C—). As noted, the number of such linking atoms, and the resultant spacing distance provided by the linking moiety Y may be modified in conjunction with other portions of the compound so as to provide desired intramolecular spacing as discussed hereinafter.

Unsaturated linking moieties Y containing double and/or triple bonds will also preferably include from about 2 to about 5 carbon atoms in the linking portion of the chain, and may include from about 1 to about 3 double or triple bonds. As seen above, one or more heteroatoms such as O, S or N may be included as substituents within the structure of the linking moiety, as for example to form an ether, thioether or secondary or tertiary amino linking structure. However, the compounds of the invention do not include those wherein Y is substituted with a primary amino group so as to form (in conjunction with the adjacent portions of the compound) an arginine (Arg) residue.

Where the linking moiety Y includes a cycloalkyl or aryl portion within its structure, such a moiety may be of the form wherein Y¹ is carbon or an O, S or N heteroatom, and Y² is an optional substituent of the form discussed above with respect to substituents on R, especially hydroxyl, amino or lower (C₁ to C₈) alkoxyl or alkyl, or other pharmaceutically suitable substituents such as nitro or halogen (especially chloro or bromo) groups. The integers p and q range independently from 0 to about 5, preferably 0 to 3, and most preferably the sum of p and q is 2. As with the linear linking groups Y described above, the choice of cyclic structures for Y (with or without appended (poly)methylene moieties) may be made in conjunction with other structures in the compound so as to achieve a desired intramolecular spacing between the guanidinyl residue and the remainder of the molecule. In this regard, the cyclic portion of each Y group depicted above contributes spacing equivalent to about 3–4 straight-chain methylene units; other cyclic or alternate linking structures may likewise be evaluated to ascertain their contribution to intramolecular spacing.

The optional group Z, where present, provides a linking function in addition to that of group Y and, therefore, may also be chosen in conjunction with the other structures in the compound to afford a desired intramolecular spacing. It is most preferred that Z be absent, particularly where the linking moiety Y contains about 5 or more linking atoms. Where present, a preferred Z group is the glycine residue (Gly), i.e., which provides a linking portion comprising 3 linking atoms (—N—C—C—). Alanine (Ala), sarcosine (Sar) and β-alanine (β-Ala) are also preferred in this position, and these provide 3 (Ala and Sar) or 4 (β-Ala) linking atoms in their structures. Each of these examples provides, as is preferred, an amino group at the left-hand terminus of Z and a carbonyl group at the right hand terminus, thereby allowing peptide-like amide bonding to each adjacent portion of the compound. Where Z is absent in the compound, it is desirable to increase the lengths of the linking portions of the Y group and/or the methylene moieties enumerated by n so as to maintain the desired intramolecular spacing.

The portion of the present compounds having the structure corresponds to the aspartic acid (Asp) amino acid residue and homologs and derivatives thereof. Where n is chosen to be 1 and $R^1$ is hydroxyl, a simple Asp residue results. (Of course, at physiological pH, the carboxylic acid hydrogen in such a residue, and in homologs thereof, will be substantially ionized to the carboxylate form.)

It is particularly preferred that $R^1$ in the above structure be of the form —OR, where R is selected from hydrogen or, more preferably, from bulky substitutents including benzyl, phenyl, and others described above with respect to $R^1$, $R^2$, $R^3$ and $R^4$.

It has been discovered in investigations relating to the invention that significant inhibition of cell adhesion may be achieved in the present compounds by providing, in a non-peptide structure as is here described, a carbonyl-containing functional group (preferably a carboxyl or ester functional group) in appropriate proximity to a guanidinyl or guanidyl-analog functional group. It is believed to be useful in this regard to maintain the intramolecular distance between such carbonyl-containing and guanidino groups within a fairly broad range that may be adjusted by using suitable choices of linking moieties Y and Z. Thus, with respect to the Asp-analog residues depicted in the formula immediately above, such proximity may be modified by selecting varying numbers of methylene moieties as enumerated by the integer n. Thus, where n is 1 (as in a simple Asp residue), the number of linking atoms in the residue separating the carbonyl functional group from the remainder of the compound (in the direction of the guanidinyl functional group) is, effectively, 3. These linking atoms are of the structure

(where the carbonyl-containing functional group on the "side chain" of the residue is depicted in brackets).

Similarly, with reference to Formula I, it is seen that the guanidinyl (or guanidinyl-analog) functional group at the left-most position in the molecule is separated from the $R^1$-attached carbonyl group by a linking structure that may be depicted as

The total number of linking atoms in the linking portion of this structure ($L^{tot}$) is equal to $L^Y + L^Z + n + 3$, where $L^Y$ and $L^Z$ are the number of linking atoms (or their equivalent) in Y and Z, respectively, and n is an integer as defined above. It is generally preferred that $L^{tot}$ be in the range of from about 7 to about 20, and most preferably from about 9 to about 12. Those practicing the invention will, in view of the present disclosure, be able to choose suitable linking groups so as to attain a desired intramolecular spacing for the product compounds.

As noted above, particularly preferred compounds include those within Y and/or Z represent simple alkylene linking groups, X= is HN= and one or more of $R^1$, $R^2$ and (if present) $R^3$ and $R^4$ are esterifying substituents. Among such preferred compounds are wherein $L^{tot}$ is, respectively, 10 ($L^Y=3$, $L^Z=3$) and 11 ($L^Y=7$, Z absent). The latter compound is especially preferred. Also preferred are compounds of the form A second group of compounds of the invention has the structure (II)

wherein

X is selected from $\underset{\|}{NR}$, $\underset{\|}{S}$ and $\underset{\|}{O}$;

Y is an unsubstituted or substituted, linear or branched linking moiety selected from saturated and unsaturated hydrocarbon groups containing from 1 to about 15 linking atoms, and optionally containing one or more heteroatoms and/or one or more cyclic structures;

$R^1$ is a substituent selected from —OR (including hydroxyl), —NR$_2$ (including —NH$_2$ and NHR), —NHNH$_2$ and —SR;

$R^5$ is selected from —R, acyl groups —COR, alkyloxycarbonyl groups of the form and from groups of the form wherein

$R^4$ and $R^6$ are substituents independently selected from groups of the form —R and acyl groups —COR, and $R^6$ may additionally be selected from alkoxycarbonyl groups of the form Z' is a suitable linking moiety, preferably selected from those of the form -continued wherein $Y^1$ comprises carbon or an O, S or N heteroatom;

$Y^2$ is an optional substituent selected from hydroxyl, amino, lower ($C_1$-$C_8$) alkoxyl and alkyl, nitro and halogen moieties;

p and q are independently integers of from 0 to about 5;

n and (where present) m are independently 1, 2 or 3;

and wherein each R is individually a pharmaceutically suitable substituent group, preferably one selected from hydrogen, from linear and branched, unsubstituted and substituted $C_1$-$C_8$ lower alkyls, $C_2$-$C_8$ alkenyls, $C_2$-$C_8$ alkynyls, $C_6$-$C^{14}$ aryls, $C_7$-$C_{14}$ alkaryls, $C_7$-$C_{14}$ aralkyls and $C_3$-$C_{14}$ cycloalkyls, from heteroatomic groups and, in the case of —$NR_2$, from cyclized groups forming (in attachment with the nitrogen atom) a 5-8 membered heterocyclic ring optionally containing oxygen, nitrogen or sulfur as a further ring heteroatom.

As with the compounds of Formula I, the compounds of the invention further include pharmaceutically acceptable base- or acid-addition salts of the compounds of Formula II. The pharmaceutical compositions of the invention include such compounds and salts thereof formulated with a pharmaceutically acceptable excipient.

It will be seen that the compounds of Formula II are structurally similar to those of Formula I except insofar as the peptide bond orientation of the groups to the right of Z' has been reversed. Accordingly, Z' is most conveniently selected to accommodate this reverse orientation by providing an amino group suitable for bonding to the carbonyl group of the succeeding reverse-orientation Asp analog. Likewise, the substituents for $R^5$ correspond (except insofar as orientation) to those given above for $R^2$ in Formula I, and also allow for suitable substitution (in the form of $R^6$) at the amino terminus appearing in $R^5$.

It is preferred in Formula II that D-enantiomeric residues be utilized in the reversed-orientation residues, i.e., in the Asp residue (to the right of Z') and, if present, in any optically active site in $R^5$. The other preferred substituents and preferred structures described above for Formula I are likewise preferred for the compounds of Formula II.

A particularly preferred $R^5$ substituent is that of the substituted or unsubstituted reverse form of serine, i.e., preferably in the D-enantiomeric form. As with the analogous $R^2$ substituent discussed above with respect to Formula I, bulky substituents (as described above) are preferred for $R^4$, and such bulky substituents are also preferred in the $R^6$ position.

The linking group Z' is preferably a lower diaminoalkane structure, e.g., of the form —$NH(CH_2)_m$—$NH$—, where m is (as defined) 1, 2 or 3. Likewise, Y is preferably a 1-to-8 carbon methylene chain as discussed above for Formula I.

As with the analogous portions of Formula I, the Y and Z' moieties in Formula II are conveniently selected so as to maintain a desired intramolecular spacing in the compound between the guanidinyl (or guanidinyl-analog) group and the carbonyl-containing group designated as —$COR^1$. In this case, the total number of linking atoms in the linking portion of Formula II ($L^{tot}$) is equal to $L^Y+L^{Z'}+n+2$, where $L^Y$ and $L^{Z'}$ are the number of linking atoms (or their equivalent) in and Z', respectively, and n is the integer as defined above. In Formula II, as with Formula I, it is generally preferred that $L^{tot}$ be in the range of from about 7 to about 20, and most preferably from about 9 to about 12.

Particularly preferred structures within the scope of Formula II include:

-continued

The following examples are given to illustrate methods whereby the present compounds may be synthesized, formulated and tested, and are not intended to limit the scope of the present invention.

EXAMPLES

Example 1

Synthesis of 8-guanidinyloctanoyl-(O-phenylmethyl)-aspartyl-(O-phenylmethyl)serine phenylmethyl ester The title compound was prepared by first dissolving 1.02 g (1.72 mmole) of the starting ester in 4 ml of 4M HCl in ethyl acetate and allowing the solution to stand for 2 hours at room temperature. After 2 hours the volatiles were removed at reduced pressure and the residue dried with toluene. The residue was dissolved in 8 ml of pyridine, 0.38 g (1.84 mmole) of dicyclohexylcarbodiimide (DCC) and 0.52 g (2.0 mmole) of the t-butyloxycarbonyl (BOC) protected acid

BOC—NH—(CH$_2$)$_7$—CO$_2$H following by addition of 0.21 g (2.0 mmole) of N-methylmorpholine. The next day the reaction mixture was filtered and the residue evaporated at reduced pressure. The residue as taken up in ethyl acetate, washed with 5% citric acid, with 5% NaHCO$_3$, dried and evaporated to give 1.16 g of red oil. Chromatography on a chromatatron with 80% ethyl acetate gave 0.72 g of white foam (55.4% yield). Crystallization from petroleum ether/ethyl acetate gave an analytical sample of the intermediate t-butyloxycarbonyl-8-aminooctanoyl-(O-phenylmethyl)-aspartyl-(O-phenylmethyl) serine phenylmethyl ester. Mp: 65–73; IR (CCl$_3$H): 3342 (NH), 1740 (ester), 1686 (amide 1), 1644 (urethane); $^1$H-NMR (CDCl$_3$): 7.18–7.40 (m, 16H, aromatic+NH), 4.86–4.94 (m, 1H, NCHCO), 4.68–4.74 (m, 1H, NCHCO), 2.16 (t, J=7.5, 2H, CH$_2$CON), 1.44 (S, 9H, t-Ba); [α]$^D$= −15.4°. Anal. calcd. for C$_{43}$H$_{53}$N$_3$O$_9$ H$_2$O: C, 66.75; H, 7.16; N, 5.43; found: C, 66.96; H, 7.28; N, 5.83.)

A 0.15 g (0.020 mmole) portion of the intermediate ester was dissolved in 5 ml of 4M HCl in ethyl acetate. After two hours the volatiles were removed at reduced pressure. The residue was suspended in 2 ml of water, 59.3 mg (0.43 mmole) of potassium carbonate, and 35.4 mg (0.28 mmole) of imine sulfonic acid was added. An immediate white precipitate formed. The next day the reaction mixture was filtered to give 0.21 g of the title compound in the form of a gummy yellow solid. The structure of the product (1) was (1)

An alternate synthesis of the title compound was performed as follows. A 0.59 g (1.0 mmole) portion of the starting ester depicted above was dissolved in 5 ml of 4M HCl in ethyl acetate and allowed to stand overnight. The next day the volatiles were removed at reduced pressure and the residue dried with toluene. An 0.21 g (1.1 mmole) portion of water soluble carbodiimide was added to the residue. A solution of 0.20 g (0.99 mmole) of the guanidinylated compound and 0.22 g (2.17 mmole) of N-methylmorpholine (NMM) in 6 ml of pyridine was then added to the residue. The next day the pyridine was removed at reduced pressure and the residue shaken with 25 mL of water. Filtration gave 0.34 g of the title compound in the form of a gummy solid which was chromatographed on a 2-inch long C-4 reverse phase column. Elution with 45:55:05 acetonitrile:water:acetic acid gave 0.16 g (23% yield) of a white gum with a k$^1$=0.66. ($^1$H-NMR (DMSO-d$_6$): 7.2–7.34 (m, 10H, aromatic), 4.95–5.10 (m, 4H, CH$_2$(C$_6$H$_5$)), 4.64–4.70 (m, 1H, NCHCO), 4.47–4.52 (m, 1H, NCHCO), 3.75 (d of d, J=9.9 & 4.1), 3.58 (d of d, J=9.9 & 3.5), 2.97 (t, J=6.8, 2H, CH$_2$-guanidine), 2.02 (t, J 7.2, 2H, CH$_2$CO).)

Example 2

General Procedure for Peptide Condensation.

As a general procedure for synthesis of the present compounds, condensations may be performed in DMF with DCC as the condensing agent. The amino acid DCHA salts are neutralized by suspending them in 1M aqueous NaHSO₄ and repeatedly extracting with ethyl acetate. The combined extracts are dried over Na₂SO₄, filtered, and evaporated. The BOC protecting groups are removed when needed by dissolving the amine in ethyl acetate and adding three equivalents of HCl in the same solvent. When the cleavage is complete, the volatiles are removed at reduced pressure and the residue dried by adding toluene and removing it again on the rotary evaporator. The hydrochloride salt is neutralized in situ by adding NMM to the DMF reaction mixture. After the condensation is complete the dicyclohexylurea is removed by filtration and the volatiles removed at reduced pressure. The peptide residue is taken up in ethyl acetate, washed with aqueous citric acid, washed with aqueous sodium bicarbonate, dried over anhydrous sodium sulfate, and evaporated at reduced pressure.

Example 3

Synthesis of

The depicted compound, 4-ureidomethyl-3-chlorophenylpropionyl aspartic acid-di-t-butyl ester (2), is prepared via the intermediate products now described.

4-Chloromethyl-3-chlorophenylpropionic acid methyl ester. A mixture of 3-chlorophenylpropionic acid methyl ester and three equivalents of methanal in concentrated aqueous HCl is stirred rapidly as HCl gas is bubbled through the mixture. After all the propionic acid has reacted, the reaction mixture is cooled and the crude benzyl chloride collected Recrystallization gives the desired intermediate compound free of the 2-chloromethyl isomer.

4-Ureidomethyl-3-chlorophenylpropionic acid methyl ester. A mixture of the above benzyl chloride and an equivalent of ferric chloride are stirred as cyanogen chloride is passed through the reaction mixture with careful exclusion of moisture. The resulting isocyanide dichloride-ferric chloride complex is not isolated, but treated with anhydrous ammonia. An extractive work-up with chloroform gives the desired urea.

4-Ureidomethyl-3-chlorophenyl propionic acid. The methyl ester from above is saponified according to standard methods using one equivalent of lithium hydroxide in methanol.

4-Ureidomethyl-3-chlorophenylpropionyl aspartic acid-di-t-butyl ester (2). A solution of the above acid and one equivalent each of DCC and the hydrochloride salt of di-t-butyl aspartic acid (Bachem Biosciences) in DMF are stirred as one equivalent of NMM is added. The next morning, the dicyclohexyl urea is removed by filtration and the filtrate evaporated at reduced pressure. The residue is taken up with ethyl acetate, washed with sequential portions of aqueous citric acid and aqueous sodium bicarbonate, dried, and evaporated to give the desired product.

Example 4

Synthesis of

The depicted compound, β-guanidinylpropionyl-glycylglutamyl(gamma-methyl ester)-threonine(β-triisopropyl silyl ether) (3), is prepared according to the following steps.

BOC-qlutamyl(gamma-methyl ester)-threonine methyl ester. The BOC-protected dipeptide is prepared according to standard procedures by sequential solution-phase coupling of BOC-Glu(gamma-methyl ester) and Thr methyl ester.

BOC-glycyl-glutamyl(gamma-methyl ester)-threonine methyl ester. This BOC-protected tripeptide is prepared from the foregoing deprotected compound by coupling BOC-Gly with DCC in DMF/NMM in the usual fashion.

FMOC-β-alanyl-glycyl-glutamyl(gamma-methyl ester)-threonine methyl ester. The BOC-protected tripeptide compound is deprotected according to the general procedure and coupled with FMOC-β-Ala in DMF/NMM using DCC activation to yield the tetrapeptide.

β-Guanidinylpropionyl-glycyl-glutamyl(gamma-methyl ester)-threonine (β-triisopropyl silyl ether) (4). Treatment of the above compound with triisopropyl silyl chloride and imidazole in DMF gives the fully protected tetrapeptide. The protected tetrapeptide above is dissolved in dichloromethane and one equivalent of piperidine is added. When cleavage of the FMOC group is complete, the volatiles are removed at reduced pressure. The resulting free amine is immediately dissolved in acetonitrile and one equivalent of aminoiminomethane sulfonic acid is added. The desired guanidine compound is collected and dried.

Example 5

Synthesis of

The title compound, 6-thioureido-4(S)-6(R)-dihydroxyhexanoyl-N-methylglycyl-β-morpholinamide-aspartyl-4-aminobutanoyl morpholine amide (4) is prepared as follows.

4-Aminobutanoic acid morpholine amide. BOC-gamma-aminobutyric acid (Bachem Biosciences) is dissolved in dry THF along with one equivalent of N-methylmorpholine. The solution is cooled to −15° C. and one equivalent of isobutylchloroformate is added dropwise. After 10 minutes at −15° C., one equivalent of morpholine is added and the resulting slurry stirred overnight with warming to room temperature. The next morning, the reaction mixture is diluted with ethyl acetate, washed with aqueous citric acid, and washed with aqueous sodium bicarbonate. The organic solution is dried with sodium sulfate, filtered, and saturated with HCl gas. After one hour, the mixture is diluted with ether and the desired amine salt collected.

BOC-L-aspartic acid (β-morpholino carboxamide) dicyclohexyl amide salt. BOC-L-aspartic acid (α-benzyl ester) (Advanced ChemTech) is dissolved in THF with an equivalent of N-methyl morpholine. The solution was cooled to −15° and one equivalent of isobutylchloroformate is added. After 10 minutes at −15°, one equivalent of morpholine is added. The reaction mixture is stirred as it warms to room temperature overnight. The reaction mixture is diluted with ethyl acetate, washed with aqueous citric acid, washed with aqueous sodium bicarbonate, dried, and filtered to give a clear solution. The organic solution is shaken with 50 psi of hydrogen and palladium on carbon until the α-benzyl ester is gone. The solution is filtered through a Celite pad and one equivalent of dicyclohexylamine is added. Ether is added and the acid salt precipitate collected.

5,6-Epoxy-3(S)-hydroxylhexanoic acid methyl ester. The 3(R)-hydroxy-5-hexanoic acid ester which is prepared by baker's yeast reduction of the 3-oxo compound as described by Bennett in *Tetrahedron Letters*, 29:4865 (1988) is dissolved in methylene chloride and allowed to react with one equivalent of meta-chloroperbenzoic acid to give the desired epoxides, as a mixture of diastereomers.

6-Amino-3(R)-5-dihydroxyl hexanoic acid ethyl ester 3-t-butyldimethylsilyl ether. The epoxides from above are treated with t-butyldimethylsilyl chloride and imidazole in DMF under the usual conditions. The crude silyl ether is dissolved in ethanol and treated with sodium azide and ammonium chloride. After the epoxide has been consumed, the reaction mixture is shaken under 50 psi of hydrogen in the presence of platinum oxide. The crude amine solution is filtered, diluted with ethyl acetate, and washed with aqueous bicarbonate solution. Drying and filtration gave the desired amine as a mixture of diasteromers.

2,2-Dimethyl-4(S)-benzyloxycarbonyl aminomethyl-1,3-dioxane acetic-6(R)-acid ethyl ester. The crude amine from the previous step is converted to its benzyloxycarbonyl derivative with benzyloxychloroformate and sodium hydroxide in water at pH 10. Ethyl acetate extraction gives the crude benzyloxycarbonate which is treated with 2-methoxypropene and a mixture of anhydrous HF and HCl. When ketalization is complete, the homogeneous aqueous solution is washed with aqueous bicarbonate solution, dried over sodium sulfate, and evaporated. The diasteromeric ketals are separated by chromatography to afford the desired compound.

2,2-Dimethyl-4(S)-thioureidomethyl-1,3-dioxane-6(R)-acetic acid ethyl ester. The Cbz-protecting group is removed from the ester from above in the standard way with hydrogenation using Pd/C in ethyl acetate. The liberated amine is reacted with silicon tetrathiocyanate as described by Nevile and McGee in *Organic Synthesis*, 5:802 (1973). The amino and 25 mole percent of silicon tetrathiocyanate is heated at 75° in toluene until the amine is consumed. Hydrolysis with aqueous 2-propanol, filtration, and evaporation of the filtrate gives a crude thiourea which is crystallized prior to the next step.

2,2-Dimethyl-4(S)-thioureidomethyl-1,3-dioxane-6(R)-acetic acid. The ester from the preceding step is saponified in aqueous ethanol with one equivalent of lithium hydroxide in the cold overnight. Careful acidification to pH 5 with 1M HCl gives the titled free acid.

6-Thioureido-4-(S)-6(R)=dihydroxyhexanoyl-N-methylglycyl-β-morpholinamideaspartyl-4-aminobutanoyl morpholine amide (4). The derivatized aspartic acid dicylohexyl amide from above is condensed with the 4-aminobutanoic acid morpholine amide, also above. After cleavage of the BOC group from the dipeptide, a second condensation with BOC-sarcosine (Bachem Biosciences) is effected. Removal of the BOC group from this tripeptide is followed by condensation with 2,2-dimethyl-4(S)-thioureidomethyl-1,3-dioxane-6(R)-acetic acid as prepared above. The protected tetrapeptide is purified by column chromatography at this point. In the final reaction, the ketal protecting group is removed with aqueous methanol and HCl to afford the desired compound 4.

Example 6

Synthesis of

The title compound, 1-(5-guanidinylpentanoyl)-4-(N,N-diethyl-D,L-valyl-D-β-benzylaspartyl)-piperazine (5) is prepared as follows.

D,L-N,N-Diethylvaline. A mixture of the commercially available 3-methyl-2-oxo-butanoic acid sodium salt and an excess of diethylamine in water is stirred and cooled as one equivalent of sodium dithionite is added slowly. When the pyruvic acid has been consumed, the pH of the solution is adjusted with concentrated HCl to the isoelectric point of the product and the reaction mixture diluted with an equal volume of alcohol. The amino acid is collected the next morning after storage in the refrigerator.

FMOC-D-Aspartic acid (β-benzyl ester). A solution of D-aspartic acid (β-benzyl ester) (Bachem Biosciences) in aqueous sodium carbonate solution is cooled to 0° C. and diluted with a one-half volume of dioxane. A solution of one equivalent of 9-fluorenylmethyl chloroformate in one volume of dioxane is added and the mixture stirred overnight as it warms to room temperature. The reaction mixture is diluted with water and extracted with ether. The aqueous phase is acidified to pH 2 and repeatedly extracted with the ethyl acetate. The combined organic extracts are washed with water, dried over MgSO₄, and evaporated to give an oil which solidifies upon standing.

FMOC-D-Aspartyl-(β-benzyl ester)-α-1-(4-butyloxycarbonyl)-piperazinyl amide. The 1-BOC derivative of piperazine is prepared as described by Carpino in *J. Org. Chem.*, 48:611 (1983) and condensed with the ester from the preceding step using the DCC general procedure. The resulting amide is purified by flash chromatography on silica gel.

5-Guanidinylpentanoic acid A solution of 5-aminopentanoic acid and one equivalent of potassium carbonate in water is stirred as one equivalent of aminoimino-methane sulfonic acid is added in portions over 15 minutes. The resulting slurry is stirred at room temperature for 24 hours. The precipitate is collected and dried to give the desired product.

1-(5-Guanidinylpentanoyl)-4-(N,N-diethyl-D,L-valyl-D-β-benzylaspartyl)-piperazine (5). The FMOC group is removed from the above piperazinyl amide intermediate with piperidine and the resulting amine dried in vacuo. Condensation by the usual DCC method with the racemic N,N-diethylvaline from above gives a dipeptide as a mixture of diasteromers which are not purified. Removal of the BOC group from the piperazine side followed by DCC coupling with the unprotected 5-guanidinylpentanoic acid, above, gives the desired tripeptide, 5. Chromatography on a reversed phase C-4 medium pressure column gives the desired compound as a mixture of diastereomers.

Example 7

Synthesis of

The depicted compound, 4-ureidobutylethylenediamino-D-glutamyl(gamma-3,5-dinitrobenzyl ester)-D-homoserinyl(benzl) -phenylacetateamide (6) is prepared as follows.

4-Ureidobutyric Acid. This intermediate is prepared according to the procedure of V. E. Marquez, J. A. Kelly and J. S. Driscoll, *J. Org. Chem.*, 45:5308 (1980).

N'-BOC-ethylenediamine. This compound is prepared according to the procedure of Callahan, *J. Med. Chem.*, 32:341 (1989).

N-BOC-D-Glutamic Acid (Y-3,5-dinitrobenzyl ester). To N-BOC-D-Glu-α-t-butyl ester (Bachem) dissolved in DMF containing 2 equivalents of triethylamine, 3,5-dinitrobenzyl chloride (Aldrich) is added slowly. After completion of the reaction the solvent is removed in vacuo and the residue is dissolved in ethyl acetate. Three equivalents of 4M HCl is added and after two hours one volume of ether is added and the N- and C-terminal deprotected D-Glu(gamma-3,5-dinitrobenyzl ester) collected. The N-terminal nitrogen is reprotected by stirring the D-Glu(gamma-3,5-dinitrobenzyl ester) and 1 equivalent of di-t-butyl-dicarbonate (Fluka) in 1:1 dioxane:2N KOH at 0° C. overnight. The mixture is concentrated and extracted thrice with ethyl acetate. The pooled ethyl acetate layers are dried with sodium sulfate, filtered and concentrated. The desired compound named above is isolated following purification by column chromatography.

BOC-D-Homoserine(Benzyl)-OH. BOC-D-Asp(OBzl)OH (Bachem Biosciences) is dissolved in ethyl acetate and treated with diazomethane in ethyl ether to produce the methyl ester. After neutralization of excess diazomethane with acetic acid, the material is subjected to medium pressure catalytic hydrogenation (Parr) with 5% Pd/C. The solution is filtered through a celite mat and concentrated to dryness. The residue is then dissolved in dry THF and treated with one equivalent of $BH_3$.dimethyl sulfide complex (Aldrich) [C. F. Lane, *Aldrichimica Acta*, 8:20 (1975)]. On completion of the side chain carboxyl reduction the mixture is diluted with ethyl acetate. The solution is washed in order with 5% citric acid, 10% sodium bicarbonate and water, dried and concentrated to dryness. The BOC-homoserine methyl ester is dissolved in DMF and treated first with one equivalent of sodium hydride, and then benzyl bromide (Aldrich). On completion of the reaction, water is added to the reaction mixture and the entire mixture evaporated to dryness. The residue is taken up in wet methanol and treated with three-fold excess lithium hydroxide until the methyl ester hydrolysis is complete. The product is purified by column chromatography to give the title compound.

4-Ureidobutyl-ethylenediamino-D-Glutamyl(gamma-3,5-dinitrobenzyl ester)-D-HomoSerinyl(Benzyl)-phenylacetateamide (6). The 4-ureidobutyric acid and one equivalent of N'-BOC-ethylenediamine from above are condensed with the general DCC coupling procedure described above. The product is deprotected with 4N HCl in ethyl acetate for 2 hours and neutralized with DIEA. The product is deprotected as usual and coupled with N-BOC-D-Glu(gamma-3,5-dinitrobenzyl ester), above, using the general DCC method. The product is deprotected and coupled to BOC-D-homoSer(Bzl), above, in an analogous way. This product is deprotected, neutralized, and coupled to the symmetric anhydride of phenylacetic acid (Aldrich). The final purification by reversed phase HPLC and lyophilization affords the desired compound, 6.

Purification of the compounds of the invention may be achieved using methods known in the art, including reversed phase HPLC size exclusion chromatography, partition chromatography on polysaccharide gel media such as Sephadex G10 or G25, or counter current distribution. One potentially important aspect in final purification is the removal of fluoride, which if present in even small amounts may alter the biological profile of the compound. Generally, ion exchange chromatography, using $AG_3$-4X acetate for example, to exchange the fluoride salt, may be used. The subject compound is dissolved in water and passed over an acetate-form resin. The eluate is collected, and lyophilized to dryness.

Salts of carboxyl groups of the product compounds may be prepared in the usual manner by contacting the compound with one or more equivalents of a desired base such as, for example, a metallic hydroxide base such as, for example, sodium hydroxide; a metal carbonate or bicarbonate base such as, for example, sodium carbonate or sodium bicarbonate; or an amine base such as, for example, triethylamine, triethanolamine, and the like. In all such procedures and in other synthetic procedures provided herein, the pH should be kept below approximately 8 in order to avoid complications such as racemization, deamidation, degradation or other undesirable side reactions.

Acid salts of the compounds may be prepared by contacting the compound with one or more equivalents of the desired inorganic or organic acid, such as, for example, hydrochloric acid, acetic acid or citric acid.

Esters or amides of carboxyl groups of the compounds may be prepared by any of the usual means known in the art for converting a carboxylic acid or precursor to an ester or amide.

Therapeutic Utility

In the practice of the therapeutic methods of the present invention, an effective amount of the active compound, including derivatives or salts thereof, or a pharmaceutical composition containing the same, as described below, is administered via any of the usual and acceptable methods known in the art, either singly or in combination with another compound or compounds of the present invention or other pharmaceutical agents such as immunosuppressants, antihistamines, corticosteroids, and the like. These compounds or compositions can thus be administered orally, sublingually, topically (e.g., on the skin or in the eyes), parenterally (e.g., intramuscularly, intravenously, subcutaneously or intradermally), or by inhalation, and in the form of either solid, liquid or gaseous dosage including tablets, suspensions, and aerosols, as is discussed in more detail below. The administration can be conducted in single unit dosage form with continuous therapy or in single dose therapy ad libitum.

Useful pharmaceutical carriers for the preparation of the pharmaceutical compositions hereof can be solids, liquids or gases; thus, the compositions can take the form of tablets, pills, capsules, powders, enterically coated or other protected formulations (such as by binding on ion exchange resins or other carriers, or packaging in lipid protein vesicles or adding additional terminal amino acids), sustained release formulations, solutions (e.g., ophthalmic drops), suspensions, elixirs, aerosols, and the like. Water, saline, aqueous dextrose, and glycols are preferred liquid carriers, particularly (when isotonic) for injectable solutions. The carrier can be selected from various oils including those of petroleum, animal, vegetable or synthetic origin, for example, peanut oil, soybean oil, mineral oil, sesame oil, and the like. Suitable pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the like. The compositions may be subjected to conventional pharmaceutical expedients such as sterilization and may contain conventional pharmaceutical additives such as preservatives, stabilizing agents, wetting or emulsifying agents, salts for adjusting osmotic pressure, buffers, and the like. Suitable pharmaceutical carriers and their formulations are described in Martin, Remington's Pharmaceutical Sciences, 15th Ed. (Mack Publishing Co., Easton 1975) (see, e.g., pp. 1405-1412, 1461-1487). Such compositions will, in general, contain an effective amount of the active compound together with a suitable amount of carrier so as to prepare the proper dosage form for proper administration to the host.

In one preferred embodiment, the therapeutic methods of the present invention are practiced when the relief of symptoms is specifically required or perhaps imminent; in another preferred embodiment, the method hereof is effectively practiced as continuous or prophylactic treatment.

In the practice of the therapeutic methods of the invention, the particular dosage of pharmaceutical composition to be administered to the subject will depend on a variety of considerations including the nature of the disease, the severity thereof, the schedule of administration, the age and physical characteristics of the subject, and so forth. Proper dosages may be established using clinical approaches familiar to the medicinal arts. It is presently believed that dosages in the range of 0.1 to 100 mg of compound per kilogram of subject body weight will be useful, and a range of 1 to 100 mg per kg generally preferred, where administration is by injection or ingestion. Topical dosages may utilize formulations containing generally as low as 0.1 mg of compound per ml of liquid carrier or excipient, with multiple daily applications being appropriate.

The compounds and therapeutic or pharmaceutical compositions of the invention are useful in the study or treatment of diseases or other conditions which are mediated by the binding of integrin receptors to ligands, including conditions involving inappropriate (i.e., excessive or insufficient) binding of cells to natural or other ligands. Such diseases and conditions include inflammatory diseases such as rheumatoid arthritis, asthma, allergy conditions, adult respiratory distress syndrome, inflammatory bowel diseases (e.g., ulcerative colitis and regional enteritis) and opthalmic inflammatory diseases; autoimmune diseases; thrombosis or inappropriate platelet aggregation conditions, and cardiovascular disease; neoplastic disease including metastasis conditions; as well as conditions wherein increased cell binding is desired, as in wound healing or prosthetic implantation situations as discussed in more detail above. Examples of "excessive" binding of cells to ligands include conditions, such as metastasis, where particular cell binding is inappropriate to the health of the subject and is sought to be eliminated to the maximum extent possible.

In addition, derivatives of the present compounds may be useful in the generation of antigens which, in turn, may be useful to generate antibodies. These antibodies will, in some cases, themselves be effective in inhibiting cell adhesion or modulating immune activity by acting as receptors for matrix proteins or other cell adhesion ligands, or, if anti-idiotypic, by acting to block cellular receptors.

EXAMPLE 8

Cell Adhesion Inhibition Assay

The following assay established the activity of the present compounds in inhibiting cell adhesion in a representative in vitro system. The assay was a competition assay in which both fibronectin and a test compound were present. Microtiter plates were first precoated with fibronectin. The test compound was then added in increasing concentrations with cells known to contain the fibronectin receptor. The plates were then washed and stained for quantitation of attached cells. The present assay directly demonstrates the anti-cell adhesion activity and modulatory activity of the present compounds. For example, by immobilizing the compound on a surface, one could adhere appropriate cells to that surface. Other cell adhesion modulation activity, and utilities pertinent thereto, will be apparent to those skilled in the art.

The cell line U937 was purchased from American Type Tissue Culture Collection. The cells were cultured in RPMI media (J. R. Scientific Company, Woodland Hills, Calif. 95695) containing 10% fetal calf serum. Fibronectin was purified from human plasma according to the procedure of Engvall, E. and Ruoslahti, E., Int. J. Cancer 20: 1–4 (1977).

Microtiter plates (96-well, Falcon) were coated overnight at 4° C. with 5 $\mu$g/ml fibronectin (FN) (for a total volume of 0.1 ml) or, as a control, 5 $\mu$g/ml bovine serum albumin (BSA) diluted in phosphate buffered saline (PBS, 0.01M $NaPO_4$ in 0.9% NaCl at pH 7.2 to 7.4). Unbound proteins were removed from plates by washing with PBS. The plates were then coated with 100 $\mu$l of PBS containing 2.5 mg/ml BSA for one hour at 37° C. This procedure is a modification of a previously published method, Cardarelli, P. M. and M. D. Pierschbacher, PNAS-USA 83: 2647–2651 (1986). The containment in the wells of functional amounts of immobilized protein has been confirmed by independent assay of fibroblast attachment and ELISA (Engvall, E., Methods Enzymol. 70: 419–439 (1980)), although the actual amount of protein bound to the plate in these assays was not determined.

A U937 culture was collected and washed two times with Hanks Balanced Salt Solution. The cells were counted and adjusted to $1.5 \times 10^6$ cells per ml in Dulbecco's Modified Eagles Medium (DMEM) plus BSA (2.5 mg/ml) for cell attachment assay. Subject compounds were then dissolved in DMEM and BSA, and the pH was adjusted to 7.4 with 7.5% sodium bicarbonate. The compounds (100 $\mu$l) were added to FN-coated wells, at 1.5, 0.75, 0.375, 0.188, 0.094, 0.047, 0.023, 0.012, 0.006 and 0.003 mg/ml final concentration and U937 cells (100 $\mu$l) were added per well. The plates were then incubated at 37° C. for 60 minutes. Following this incubation, the plates were washed once with PBS. Attached cells were fixed with 3% paraformaldehyde in PBS and stained with 0.5% toluidine blue in 3.7% formaldehyde. The cells were stained overnight at room temperature and the optical density at 590 nm of toluidine blue-stained cells was determined using a vertical pathway spectrophotometer to quantitate attachment (VMAX Kinetic Microplate Reader, Molecular Devices, Menlo Park, Calif. 94025).

Figure 1:
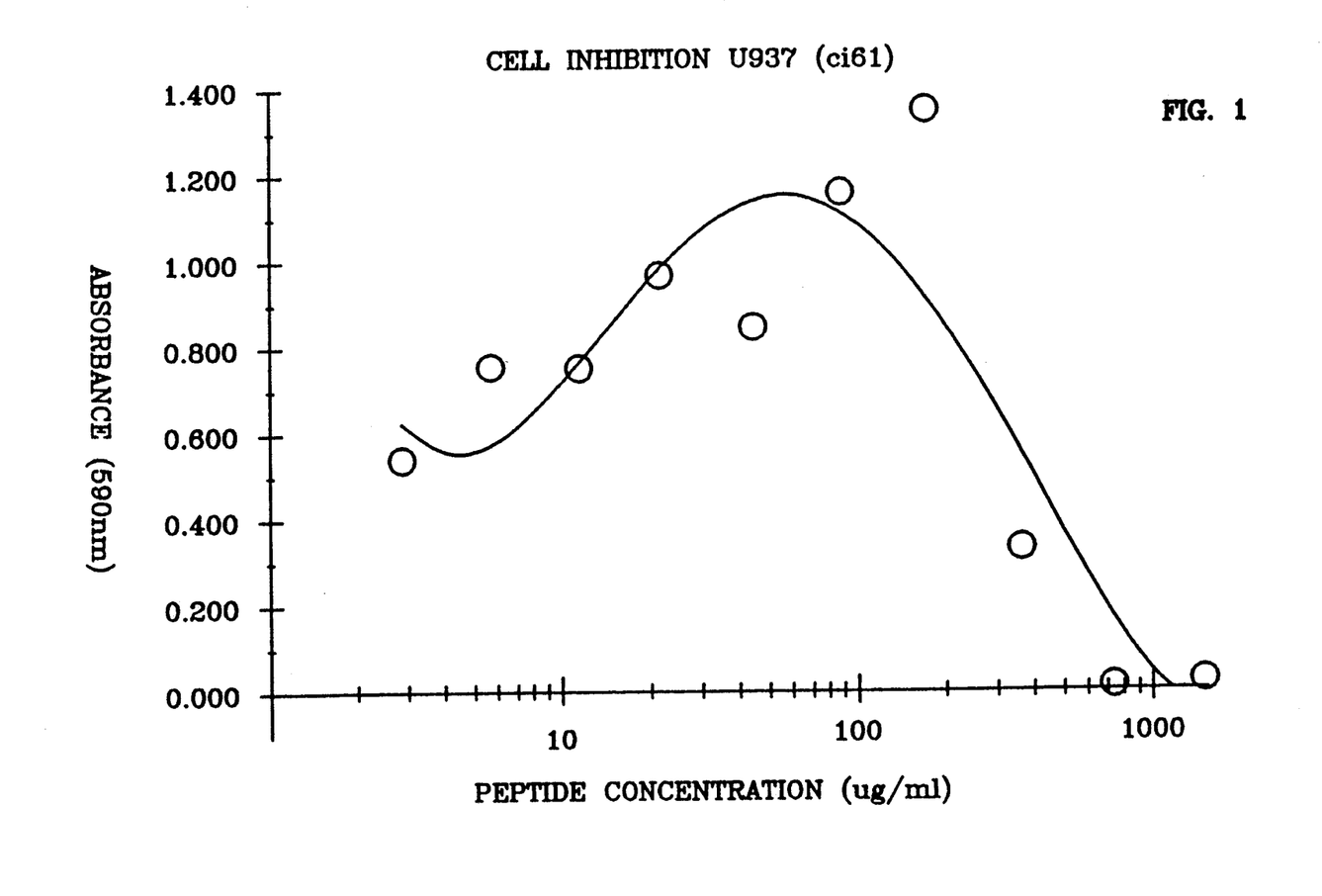
The accompanying figure is a graphical representation showing cell adhesion inhibition by a representative guanidinyl compound of the invention, 8-guanidinyloctanoyl-(O-phenylmethyl)-aspartyl-(O-phenylmethyl)serine phenylmethyl ester.

Results. The table below shows the results of the cell adhesion inhibition assay for representative compounds of the invention. Potency is expressed in $\mu$M units. The accompanying figure is a diagram representing the curve of cell adhesion inhibition for the compound

ACTIVITY OF COMPOUNDS IN THE U937 FIBRONECTIN ADHESION ASSAY

| Peptide | IC$_{50}$, µM |
|---|---|
| | 345 |
| | 2400 |
| | 2500 |

In addition, the compounds $$H_2N-\overset{NH}{\underset{\|}{C}}-NH-(CH_2)_2-\overset{O}{\underset{\|}{C}}-Gly-Asp-Ser \text{ and}$$

$$H_2N-\overset{NH}{\underset{\|}{C}}-NH-(CH_2)_4-\overset{O}{\underset{\|}{C}}-Gly-Asp-Ser$$

were also synthesized and tested in the cell adhesion inhibition assay described above. Specific activity levels were not established inasmuch as the IC$_{50}$ of the compounds was determined to be in excess of 1.5 mg/ml. Thus, although such compounds are believed to be active as cell adhesion modulators at higher dosage levels, they are presently not as highly preferred as the compounds exemplified above.

The foregoing examples are given to enable those skilled in the art to more fully understand and practice the present invention. They should not be construed as a limitation upon the scope of the invention, which is set forth in the appended claims, but merely as being illustrative and representative thereof.

What is claimed is:

1. A compound of the formula:

$$\overset{X}{\underset{\|}{H_2N-C}}-NH-Y-\overset{O}{\underset{\|}{C}}(\!\!-Z\!\!-\!\!)NH-\overset{O=CR^1}{\underset{\underset{O}{\|}}{\overset{(CH_2)_n}{\underset{|}{CH-C-R^2}}}} \quad (I)$$

and pharmaceutically acceptable salts thereof, wherein

X is selected from $\overset{NR}{\underset{\|}{}}$, $\overset{S}{\underset{\|}{}}$ and $\overset{O}{\underset{\|}{}}$;

Y is an unsubstituted or substituted, linear or branched linking moiety selected from saturated and unsaturated hydrocarbon groups containing from 1 to about 15 linking atoms, Z is optional and, where present, is selected from Gly, Ala, Sar and β-Ala;

one of R$^1$ and R$^2$ is selected from —OR (including hydroxyl), —NR$_2$ (including —NH$_2$ and —NHR), —NHNH$_2$ and —SR, and the other is selected from $$-\underset{(OR^4)}{Ser}-R^3, -\underset{(OR^4)}{Thr}-R^3, -Ala-R^3, -Leu-R^3,$$

$$-Ile-R^3, -Nle-R^3, -NH-\underset{\underset{O}{\|}}{\overset{(CH_2)_m-OR^4}{\underset{|}{CH-CR^3}}},$$

$$-NH-(CH_2)_m-OR^4 \text{ and } -NH-(CH_2)_m-\overset{O}{\underset{\|}{C}}-R^3$$

wherein

R$^3$ is a substituent selected from —OR (including hydroxyl), —NR$_2$ (including —NH$_2$ and —NHR), —NHNH$_2$ and —SR, and R$^4$ is a substituent selected from groups of the form —R and acyl groups —COR;

n and (where present) m are independently 1, 2 or 3;

and wherein each R group is individually a pharmaceutically suitable substituent group selected from hydrogen, from linear and branched, unsubstituted and substituted $C_1$-$C_8$ lower alkyls, $C_2$-$C_8$ alkenyls, $C_2$-$C_8$ alkynyls, $C_6$-$C_{14}$ aryls, $C_7$-$C_{14}$ alkaryls, $C_7$-$C_{14}$ aralkyls and $C_3$-$C_{14}$ cycloalkyls, from heteroatomic groups and, in the case of —$NR_2$, from cyclized groups forming (in attachment with the nitrogen atom) a 5-8 membered heterocyclic ring optionally containing oxygen, nitrogen or sulfur as a further ring heteroatom.

2. The compound of claim 1 wherein each R group is independently selected from hydrogen and from unsubstituted and substituted lower alkyl and single-ring aryl hydrocarbon moieties.

3. The compound of claim 1 wherein at least one R group is independently selected from unsubstituted and substituted single-ring aryl hydrocarbon moieties.

4. The compound of claim 1 wherein $R^1$ and $R^3$ are of the form —OR.

5. The compound of claim 4 wherein each R group is independently selected from hydrogen and from unsubstituted and substituted lower alkyl and single-ring aryl hydrocarbon moieties.

6. The compound of claim 4 wherein each R group in $R^3$ and, if present, $R^4$ is independently selected from unsubstituted and substituted single-ring aryl hydrocarbon moieties.

7. The compound of claim 1 wherein Y is a hydrocarbon chain from 1 to about 8 linking atoms.

8. A compound of claim 7 selected from the group consisting of and pharmaceutically acceptable salts thereof, where r is an integer of from 1 to about 8 and s is an integer of from 1 to about 5.

9. A compound of claim 7 selected from the group consisting of and pharmaceutically acceptable salts thereof.

10. A method of modulating cell adhesion comprising administering, in a system including cells expressing an integrin receptor, an amount effective to modulate the adhesion of said cells of a compound of claim 1.

11. The method of claim 10 wherein said cells express a receptor for fibronectin.

12. The method of claim 10 wherein said system is a mammalian system characterized by an excessive or inadequate level of cell adhesion.

* * * * *